(12) United States Patent
Li

(10) Patent No.: US 10,510,809 B2
(45) Date of Patent: Dec. 17, 2019

(54) OLED DISPLAY

(71) Applicant: Wuhan China Star Optoelectronics Technology Co., Ltd., Wuhan (CN)

(72) Inventor: Xianjie Li, Wuhan (CN)

(73) Assignee: WUHAN CHINA STAR OPTOELECTRONICS TECHNOLOGY CO., LTD., Wuhan, Hubei (CN)

( * ) Notice: Subject to any disclaimer, the term of this patent is extended or adjusted under 35 U.S.C. 154(b) by 361 days.

(21) Appl. No.: 15/505,112

(22) PCT Filed: Dec. 30, 2016

(86) PCT No.: PCT/CN2016/113323
§ 371 (c)(1),
(2) Date: Feb. 20, 2017

(87) PCT Pub. No.: WO2018/119966
PCT Pub. Date: Jul. 5, 2018

(65) Prior Publication Data
US 2019/0157352 A1    May 23, 2019

(30) Foreign Application Priority Data
Dec. 26, 2016    (CN) .......................... 2016 1 1221433

(51) Int. Cl.
*H01L 51/00*    (2006.01)
*H01L 27/32*    (2006.01)
(Continued)

(52) U.S. Cl.
CPC .............. *H01L 27/322* (2013.01); *C07F 7/24* (2013.01); *H01L 27/3211* (2013.01);
(Continued)

(58) Field of Classification Search
CPC .............. H01L 27/322; H01L 27/3211; H01L 27/3244; H01L 51/4206; H01L 51/5036;
(Continued)

(56) References Cited

U.S. PATENT DOCUMENTS

2013/0082589 A1* 4/2013 So ....................... H01L 51/5036
                                                          313/504
2014/0374697 A1* 12/2014 Liu ....................... H01L 51/502
                                                          257/13
(Continued)

FOREIGN PATENT DOCUMENTS

| CN | 101351829 A | 1/2009 |
| CN | 103474451 A | 12/2013 |
| CN | 104388089 A | 3/2015 |

*Primary Examiner* — Victor A Mandala
*Assistant Examiner* — Colleen E Snow
(74) *Attorney, Agent, or Firm* — Leong C. Lei

(57) ABSTRACT

The present invention provides an OLED display, comprising a substrate, a thin film transistor layer, a blue light emitting layer, a cover plate and a color conversion layer; wherein the color conversion layer comprises a plurality of red conversion units and green conversion units, and both materials of the red conversion units and the green conversion units are organic metal halide perovskite materials; the blue light emitted by the blue light OLED correspond to the red, the green and the blue sub pixel regions, and respectively converted into red light by the red conversion units to emit, converted into green light by the green conversion units to emit and emitted through the cover plate, directly to obtain the red, green, blue lights of high color saturation to realize the color display of the high color gamut.

16 Claims, 2 Drawing Sheets

(51) Int. Cl.
    *H01L 51/50*     (2006.01)
    *H01L 51/52*     (2006.01)
    *H01L 51/42*     (2006.01)
    *C07F 7/24*     (2006.01)

(52) U.S. Cl.
    CPC ...... *H01L 51/4206* (2013.01); *H01L 51/5036* (2013.01); *H01L 51/5092* (2013.01); *H01L 51/524* (2013.01); *H01L 27/3244* (2013.01); *H01L 51/5056* (2013.01); *H01L 51/5072* (2013.01); *H01L 51/5218* (2013.01); *H01L 51/5234* (2013.01); *H01L 2251/301* (2013.01)

(58) Field of Classification Search
    CPC ............. H01L 51/5092; H01L 51/5218; H01L 51/5234; H01L 51/524; C07F 7/24
    See application file for complete search history.

(56) References Cited

U.S. PATENT DOCUMENTS

2016/0293866 A1* 10/2016 Ishibashi ................ C09K 11/06
2017/0152608 A1*  6/2017 Jin ........................... C30B 7/14
2017/0365794 A1* 12/2017 Park ..................... H01L 51/0072

\* cited by examiner

OLED DISPLAY

FIELD OF THE INVENTION

The present invention relates to a display technology field, and more particularly to an OLED display.

BACKGROUND OF THE INVENTION

The Organic Light Emitting Diode (OLED) display is a display technology which has great prospects for development. It does not only possess extremely excellent display performance but also properties of self-illumination, simple structure, ultra thin, fast response speed, wide view angle, low power consumption and capability of realizing flexible display, and therefore is considered as "dream display". At present, the OLED display has got the favor of the major display manufacturers, and becomes the third generation display after the Cathode Ray Tube (CRT) and the Liquid Crystal Display (LCD).

So far, the ratio of the OLED used in the apparatuses, such as the cell phone and the tablet becomes higher and higher. The main technical spirit is an OLED display utilizing the Red, Green, Blue (RGB), three primary colors for emission, and utilizing the Fine Metal Mask (FMM) to manufacture the red, green, blue sub pixels aligned Side by Side (SBS). Along with the higher and higher requirement for the resolution in the market, this technology appears more and more inadequate due to the restriction of FMM accuracy.

Another method to realize the full color display is white light OLED+RGB color filters (CF) technology. The mature CF skill is used and it will not be restricted by the FMM accuracy, and thus, can be used for manufacturing the high resolution OLED display. However, the saturation of the three primary colors is lower, and the display color gamut is not wide enough (NTSC color gamut<90%).

There is one more solution for realizing the full color is based on the blue light OLED, and with the help of the Color conversion method (CCM) of the green light and the red light. The blue light excites the red, green light materials to make them emit lights to obtain the red, green, blue, three primary colors to realize the color display. Nevertheless, most of the CCM materials for now are organic fluorescent materials, and the color saturation is low, and the display color gamut is not wide enough (NTSC color gamut<90%).

SUMMARY OF THE INVENTION

An objective of the present invention is to provide an OLED display having simple manufacture process and fine properties of high resolution, wide color gamut, good light effect and high stability.

For realizing the aforesaid objective, the present invention provides an OLED display, comprising a substrate, a thin film transistor layer formed on the substrate, a blue light OLED formed on the thin film transistor layer, a cover plate located on the blue light OLED and laminated with the substrate and a color conversion layer formed at an inner side of the cover plate;

the blue light OLED comprising an anode, a hole injection layer, a hole transporting layer, a blue light emitting layer, an electron transport layer, an electron injection layer and a cathode which are stacked up from bottom to top in order;

the color conversion layer comprising a plurality of red conversion units and green conversion units which are separately located;

blue light emitted by the blue light emitting layer being respectively converted into red light by the red conversion units to emit, converted into green light by the green conversion units to emit and emitted through the cover plate, directly to realize color display;

wherein both materials of the red conversion units and the green conversion units are organic metal halide perovskite materials.

A constitutional formula of the organic metal halide perovskite material is $CH_3NH_3PbA_3$, and A is a combination of one or more elements of Cl, Br and I.

Both materials of the red conversion units and the green conversion units are a combination of one or more of the organic metal halide perovskite materials;

the red conversion units and the green conversion units are single layer or multi layer structures;

a thickness of the red conversion units and the green conversion units is 10 nm-200 nm.

A material of the red conversion units is $CH_3NH_3Pb(I_{0.9}Br_{0.1})_3$, and a material of the green conversion units is $CH_3NH_3PbBr_3$.

A material of the blue light emitting layer is manufactured by doping a guest material in a host material, wherein a doping quality ratio of the host material and the guest material is 1:0.01-1;

the guest material is a blue light organic fluorescent material, and the host material is an anthracene derivative or a wide band gap organic material; or the guest material is blue light organic phosphorescent material, and the host material is a wide band gap organic material.

Both materials of the substrate and the cover plate are glass or a flexible material.

The anode is an opaque reflective type anode, comprising two conductive oxide layers and a reflective metal layer between the two conductive oxide layers, wherein a film thickness of the reflective metal layer is 50 nm-200 nm; a film thickness of the conductive oxide layers is 10 nm-50 nm.

The cathode is a nonopaque transparent cathode; a material of the cathode is a low work function metal or an alloy of low work function metal, and a film thickness is 10 nm-20 nm; or a material of the cathode is conductive oxide, and a film thickness is 10 nm-200 nm.

A material of the hole injection layer is an organic small molecule hole injection material, a polymer hole injection material or a metal oxide hole injection material, and a film thickness is 1 nm-100 nm;

a material of the hole transporting layer is an organic small molecule hole transporting material or a polymer hole transporting material, and a film thickness is 10 nm-100 nm;

a material of the electron transporting layer is a metal complex material or an imidazole electron transport material, and a film thickness is 10 nm-100 nm;

a material of the electron injection layer is metal complex, alkali metal, alkali metal salts, alkali earth metal or alkali earth metal salts, and a film thickness is 0.5 nm-10 nm.

The OLED display further comprises a sealant bonding the substrate and the cover plate.

The present invention further provides an OLED display, comprising a substrate, a thin film transistor layer formed on the substrate, a blue light OLED formed on the thin film transistor layer, a cover plate located on the blue light OLED and laminated with the substrate and a color conversion layer formed at an inner side of the cover plate;

the blue light OLED comprising an anode, a hole injection layer, a hole transporting layer, a blue light emitting layer, an electron transport layer, an electron injection layer and a cathode which are stacked up from bottom to top in order;

the color conversion layer comprising a plurality of red conversion units and green conversion units which are separately located;

blue light emitted by the blue light emitting layer being respectively converted into red light by the red conversion units to emit, converted into green light by the green conversion units to emit and emitted through the cover plate, directly to realize color display;

both materials of the red conversion units and the green conversion units being organic metal halide perovskite materials;

the OLED display further comprising a sealant bonding the substrate and the cover plate;

wherein both materials of the substrate and the cover plate are glass or a flexible material.

The benefits of the present invention are: the present invention provides an OLED display, comprising a substrate, a thin film transistor layer, a blue light emitting layer, a cover plate and a color conversion layer; wherein the color conversion layer comprises a plurality of red conversion units and green conversion units, and both materials of the red conversion units and the green conversion units are organic metal halide perovskite materials; the blue light emitted by the blue light OLED correspond to the red, the green and the blue sub pixel regions, and respectively converted into red light by the red conversion units to emit, converted into green light by the green conversion units to emit and emitted through the cover plate, directly to obtain the red, green, blue lights of high color saturation to realize the color display of the high color gamut. Meanwhile, all the red, the green and the blue sub pixel regions correspond to the blue light OLED of the same structure. The fine mask is not required to use as manufacturing the OLED display, which can effectively promote the resolution and stability of the OLED display. The manufacture process is simple.

BRIEF DESCRIPTION OF THE DRAWINGS

In order to better understand the characteristics and technical aspect of the invention, please refer to the following detailed description of the present invention is concerned with the diagrams, however, provide reference to the accompanying drawings and description only and is not intended to be limiting of the invention.

In drawings.

DETAILED DESCRIPTION OF PREFERRED EMBODIMENTS

For better explaining the technical solution and the effect of the present invention, the present invention will be further described in detail with the accompanying drawings and the specific embodiments.

Figure 1:
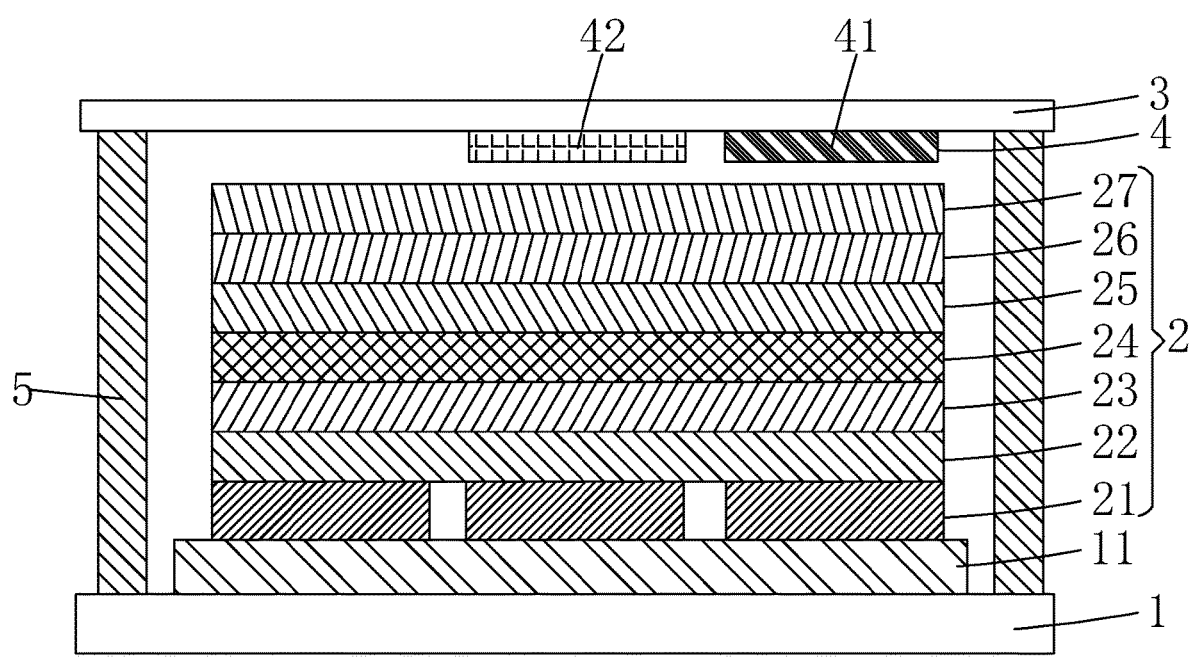
FIG. 1 is a structure diagram of an OLED display of the present invention.

Please refer to FIG. 1. The present invention provides an OLED display comprising a plurality of red sub pixel regions, green sub pixel regions and blue sub pixel regions; and comprising a substrate 1, a thin film transistor layer 11 formed on the substrate 1, a blue light OLED 2 formed on the thin film transistor layer 11, a cover plate 3 located on the blue light OLED 2 and laminated with the substrate 1, a color conversion layer 4 formed at an inner side of the cover plate 3, and a sealant 5 bonding the substrate 1 and the cover plate 3.

The blue light OLED 2 comprises an anode 21, a hole injection layer 22, a hole transporting layer 23, a blue light emitting layer 24, an electron transport layer 25, an electron injection layer 26 and a cathode 27 which are stacked up from bottom to top in order.

The color conversion layer 4 comprises a plurality of red conversion units 41 and green conversion units 42 which are separately located, and respectively correspond to the red sub pixel regions and the green sub pixel regions.

blue light emitted by the blue light emitting layer being respectively converted into red light by the red conversion units to emit, converted into green light by the green conversion units to emit and emitted through the cover plate, directly to realize color display The organic metal halide perovskite material is a new type of high efficiency semiconductor light emitting material which possesses the advantages of narrow emission spectrum and high color purity, and is very suitable for being a new type CCM material to manufacture the display screen of wide color gamut (NTSC color gamut>100%). Such type of material possesses the advantages of optical properties of inorganic semiconductor and low temperature film formation of organic material, and can realize the tunable wavelength by changing the composition thereof.

In the present invention, both materials of the red conversion units 41 and the green conversion units 42 are organic metal halide perovskite materials; a constitutional formula of the organic metal halide perovskite material is $CH_3NH_3PbA_3$, and A is a combination of one or more elements of Cl, Br and I.

The OLED display of the present invention has fine properties of high resolution, wide color gamut, good light effect and high stability and the manufacture process is simple; the reason is that as performing display, the blue light of high brightness, high color saturation can be obtained with the blue light OLED 2, and with the merits of the high color saturation luminescence of the organic metal halide perovskite material, the red light and the green light of high color saturation can be obtained with the red conversion units 41 and the green conversion units 42 of the color conversion layer 4. Therefore, the display gamut of the OLED display utilizing such structure can exceed 100% of the NTSC color gamut; more importantly, the red, green, blue, three primary colors as used for display all come from the blue light OLED 2 of the same structure, and thus to prevent the use of the fine mask in the manufacture process, and is very beneficial for promoting the resolution of the OLED display and the product yield.

Specifically, both materials of the red conversion units 41 and the green conversion units 42 can be one organic metal halide perovskite material, or can be a combination of a plurality of organic metal halide perovskite materials.

Specifically, the red conversion units 41 and the green conversion units 42 can be single layer or multi layer structures.

Specifically, both the red conversion units 41 and the green conversion units 42 are manufactured by a wet film forming method.

Specifically, a thickness of the red conversion units 41 and the green conversion units 42 is 10 nm-200 nm.

Specifically, a material of the blue light emitting layer 24 is manufactured by doping a guest material in a host material, wherein a doping quality ratio of the host material and the guest material is 1:0.01-1. The blue light emitting layer 24 can be manufactured by a vacuum evaporation or a liquid phase film method.

The guest material can be a blue light organic fluorescent material, such as BD3 (1-(10-(4-methoxyphenyl)anthracen-9-yl)-4-(10-(4-cyanophenyl)anthracen-9-yl)benzene), or can be an organic phosphorescent material. When the guest material is a blue light organic fluorescent material, the host material can be an anthracene derivative, such as MADN (2-Methyl-9,10-bis(naphthalen-2-yl)anthracene), or can be a wide band gap organic material, such as mCP (1,3-Di-9-carbazolylbenzene), CBP(4,4'-Bis(N-carbazolyl)-1,1'-biphenyl); when the guest material is a blue light organic phosphorescent material, the host material is a wide band gap organic material, such as mCP, CBP.

The molecular architecture of the BD3 is

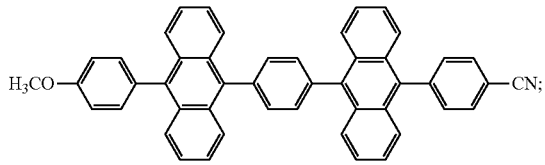 [SMILES: COc1ccc(-c2c3ccccc3c(-c3ccc(-c4c5ccccc5c(-c5ccc(C#N)cc5)c5ccccc45)cc3)c3ccccc23)cc1]

The molecular architecture of the CBP is

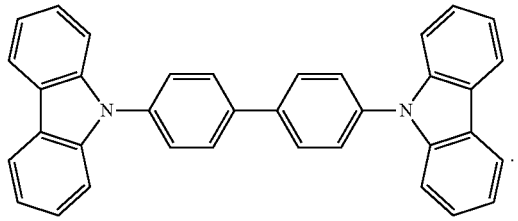 [SMILES: c1ccc2c(c1)c1ccccc1n2-c1ccc(-c2ccc(-n3c4ccccc4c4ccccc43)cc2)cc1]

Specifically, both materials of the substrate 1 and the cover plate 3 are glass or a flexible material.

Specifically, the anode 21 is an opaque reflective type anode, comprising two conductive oxide layers and a reflective metal layer between the two conductive oxide layers, which is a structure of conductive oxide/reflective metal/conductive oxide, wherein a material of the reflective metal layer is a high work function metal, such as gold (Au), silver (Ag), aluminum (Al), copper (Cu) or an alloy of the foregoing high work function metals, and a film thickness is 50 nm-200 nm; a material of the conductive oxide layer is Indium Tin Oxide (ITO), Indium Zinc Oxide (IZO), and a film thickness is 10 nm-50 nm; specifically, the anode 21 can be manufactured by a method of sputter or vacuum evaporation.

Specifically, the cathode 27 is a nonopaque transparent cathode; a material of the cathode 27 can be a low work function metal, such as lithium (Li), magnesium (Mg), calcium (Ca), strontium (Sr), lanthanum (La), cerium (Ce), europium (Eu), ytterbium (Yb), cesium (Cs), rubidium (Rb) or an alloy of the foregoing low work function metals, and the aforesaid cathode materials can be solo used, or two or more combinations can be utilized, and a film thickness is 10 nm-20 nm; or a material of the cathode 27 also can be conductive oxide, such as ITO, IZO, and a film thickness is 10 nm-200 nm, and specifically, the cathode 27 can be manufactured by a method of vacuum evaporation.

Specifically, a material of the hole injection layer 22 can be an organic small molecule hole injection material, such as HATCN (Dipyrazino[2,3-f:2',3'-h]quinoxaline-2,3,6,7,10,11-hexacarbonitrile), or can be a polymer hole injection material, such as PEDT:PSS (poly(ethylenedioxythiophene):polystyrene sulphonate) or a metal oxide hole injection material, such as molybdenum trioxide ($MoO_3$), and a film thickness of the hole injection layer 22 is 1 nm-100 nm, and specifically, the hole injection layer 22 can be manufactured by vacuum evaporation or a liquid phase film method.

The chemical architecture of the HATCN is

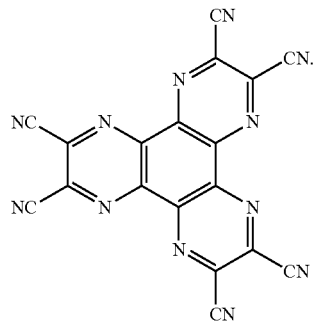 [SMILES: N#Cc1nc2c3nc(C#N)c(C#N)nc3c3nc(C#N)c(C#N)nc3c2nc1C#N]

Specifically, a material of the hole transporting layer 23 can be an organic small molecule hole transporting material, such as NPB (N,N'-Bis-(1-naphthalenyl)-N,N'-bis-phenyl-(1,1'-biphenyl)-4,4'-diamine, TAPC (4,4'-yclohexylidenebis [N,N-bis(p-tolyl)aniline]) or can be a polymer hole injection material, such as Poly-TPD (Poly[bis(4-phenyl)(4-butylphenyl)amine]) and a film thickness of the hole transporting layer 23 is 10 nm-100 nm, and specifically, the hole transporting layer 23 can be manufactured by vacuum evaporation or a liquid phase film method.

The chemical architecture of the TAPC is

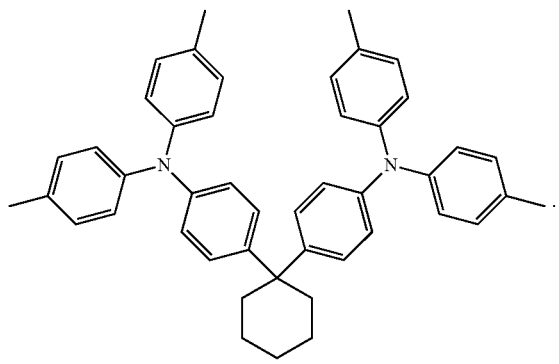

Specifically, a material of the electron transporting layer 25 can be a metal complex material, such as Alq3 (tris(8-quinolinolato) aluminum) or can be an imidazole electron transport material, such as TPBi (1,3,5-Tris(1-phenyl-1H-benzimidazol-2-yl)benzene), and a film thickness of the electron transporting layer 25 is 10 nm-100 nm, and electron transporting layer 25 can be manufactured by vacuum evaporation or a liquid phase film method.

The chemical architecture of the TPBi is

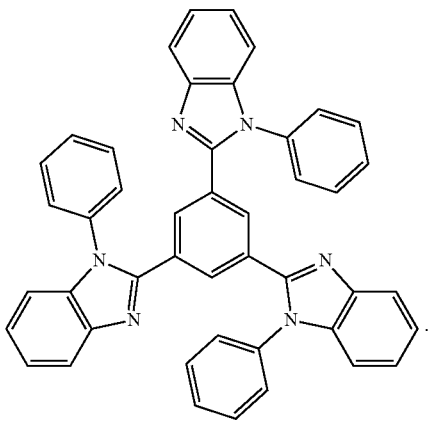 [SMILES: c1ccc(-n2c(-c3cc(-c4nc5ccccc5n4-c4ccccc4)cc(-c4nc5ccccc5n4-c4ccccc4)c3)nc3ccccc32)cc1]

Specifically, a material of the electron injection layer 26 can be metal complex, such as 8-hydroxy quinoline lithium (Liq), or can be alkali metal or the salts thereof, such as lithium (Li), sodium (Na), potassium (K), rubidium (Rb), cesium (Cs), lithium fluoride (LiF), lithium carbonate ($Li_2CO_3$), lithium chloride (LiCl), sodium fluoride (NaF), sodium carbonate ($Na_2CO_3$), sodium chloride (NaCl), cesium fluoride (CsF), cesium carbonate ($Cs_2CO_3$), Cesium chloride (CsCl), or can be alkali earth metal or the salts thereof, such as magnesium (Mg), calcium (Ca), strontium (Sr), barium (Ba), calcium fluoride ($CaF_2$), calcium carbonate ($CaCO_3$), strontium fluoride ($SrF_2$), strontium carbonate ($SrCO_3$), barium fluoride ($BaF_2$), barium carbonate ($BaCO_3$), and a film thickness of the electron injection layer 26 is 0.5 nm-10 nm.

In one preferred embodiment of the present invention, the anode 21 is an ITO/Ag/ITO structure, and a film thickness of the Ag layer thereof is 100 nm, and both the film thicknesses of the ITO layers at the two sides of the Ag layer are 15 nm; a material of the hole injection layer 22 is HATCN, and a film thickness is 10 nm; a material of the hole transporting layer 23 is TAPC, and a film thickness is 30 nm; a material of the blue light emitting layer 24 is manufactured by doping CBP with BD3, wherein the mass contents of CBP and BD3 respectively are 95% and 5%, and a film thickness of the blue light emitting layer 24 is 25 nm; a material of the electron transporting layer 25 is TPBi, and a film thickness is 30 nm; a material of the electron injection layer 26 is LiF, and a film thickness is 1 nm; the cathode 27 is an alloy of Ag and Mg, wherein the mass contents of Ag and Mg respectively are 10% and 90%, and a film thickness of the cathode 27 is 20 nm; a material of the red conversion units 41 is $CH_3NH_3Pb(I_{0.9}Br_{0.1})_3$(Methylammonium lead Bromide Iodide), and a film thickness is 50 nm; a material of the green conversion units 42 is $CH_3NH_3PbBr_3$ (Methylammonium lead Bromide), and a film thickness is 50 nm; furthermore, the anode 21 is manufactured by a method of sputter, and all the hole injection layer 22, the hole transporting layer 23, the blue light emitting layer 24, the electron transporting layer 25, the electron injection layer 26 and the cathode 27 are manufactured by a method of vacuum evaporation, and both the red conversion units 41 and the green conversion units 42 are manufactured by a wet film forming method.

Figure 2:
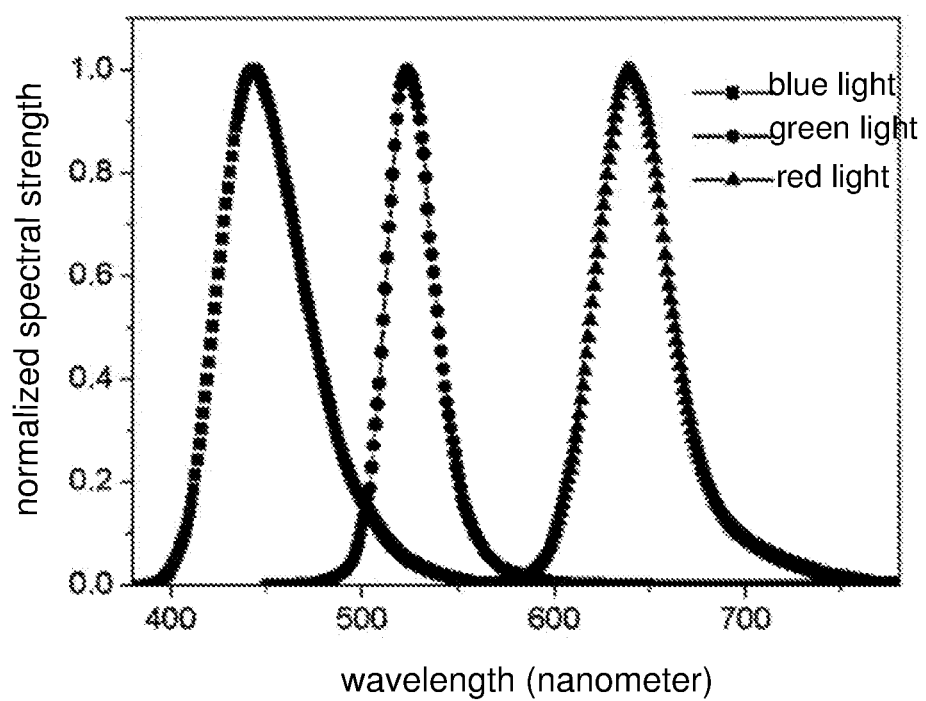
FIG. 2 is a normalized spectral distribution curve diagram of red light, green light, blue light of one preferred embodiment according to the OLED display of the present invention.

According to the experiment measurement analysis, the chroma data table of the OLED display shown in table 1, and the normalized spectral distribution curve diagram of red light, green light, blue light shown in FIG. 2 can be obtained. The aforesaid preferred embodiment combines the blue light OLED 2 and the color conversion layer 4 of organic metal halide perovskite material to be able to obtain the red, green, blue three color lights of high saturation. The NTSC color gamut of the OLED display can reach up to 120.2%.

TABLE 1

| primary color light | CIE chroma (x) | CIE chroma (y) | NTSC color gamut (%) |
|---|---|---|---|
| red light | 0.697 | 0.303 | 120.2 |
| green light | 0.170 | 0.757 | |
| blue light | 0.148 | 0.054 | |

In conclusion, the present invention provides an OLED display, comprising a substrate, a thin film transistor layer, a blue light emitting layer, a cover plate and a color conversion layer; wherein the color conversion layer comprises a plurality of red conversion units and green conversion units, and both materials of the red conversion units and the green conversion units are organic metal halide perovskite materials; the blue light emitted by the blue light OLED correspond to the red, the green and the blue sub pixel regions, and respectively converted into red light by the red conversion units to emit, converted into green light by the green conversion units to emit and emitted through the cover plate, directly to obtain the red, green, blue lights of high color saturation to realize the color display of the high color gamut. Meanwhile, all the red, the green and the blue sub pixel regions correspond to the blue light OLED of the same structure. The fine mask is not required to use as manufacturing the OLED display, which can effectively promote the resolution and stability of the OLED display. The manufacture process is simple.

Above are only specific embodiments of the present invention, the scope of the present invention is not limited to this, and to any persons who are skilled in the art, change or replacement which is easily derived should be covered by the protected scope of the invention. Thus, the protected scope of the invention should go by the subject claims.

What is claimed is:
1. An OLED display, comprising a substrate, a thin film transistor layer formed on the substrate, a blue light OLED formed on the thin film transistor layer, a cover plate located on the blue light OLED and laminated with the substrate and a color conversion layer formed at an inner side of the cover plate;
  the blue light OLED comprising an anode, a hole injection layer, a hole transporting layer, a blue light emitting layer, an electron transport layer, an electron injection layer and a cathode which are stacked up from bottom to top in order;
  the color conversion layer comprising a plurality of red conversion units and green conversion units which are separately located;
  blue light emitted by the blue light emitting layer being respectively converted into red light by the red conversion units to emit, converted into green light by the green conversion units to emit and emitted through the cover plate, directly to realize color display;
  wherein both materials of the red conversion units and the green conversion units are organic metal halide perovskite materials;

wherein a material of the red conversion units is $CH_3NH_3Pb(I_{0.9}Br_{0.1})_3$, and a material of the green conversion units is $CH_3NH_3PbBr_3$.

2. The OLED display according to claim 1, wherein a constitutional formula of the organic metal halide perovskite material is $CH_3NH_3PbA_3$, and A is a combination of one or more elements of Cl, Br and I.

3. The OLED display according to claim 1, wherein both materials of the red conversion units and the green conversion units are a combination of one or more of the organic metal halide perovskite materials;
the red conversion units and the green conversion units are single layer or multi layer structures;
a thickness of the red conversion units and the green conversion units is 10 nm-200 nm.

4. The OLED display according to claim 1, wherein a material of the blue light emitting layer is manufactured by doping a guest material in a host material, wherein a doping quality ratio of the host material and the guest material is 1:0.01-1;
the guest material is a blue light organic fluorescent material, and the host material is an anthracene derivative or a wide band gap organic material; or
the guest material is blue light organic phosphorescent material, and the host material is a wide band gap organic material.

5. The OLED display according to claim 1, wherein both materials of the substrate and the cover plate are glass or a flexible material.

6. The OLED display according to claim 1, wherein the anode is an opaque reflective type anode, comprising two conductive oxide layers and a reflective metal layer between the two conductive oxide layers, wherein a film thickness of the reflective metal layer is 50 nm-200 nm; a film thickness of the conductive oxide layers is 10 nm-50 nm.

7. The OLED display according to claim 1, wherein the cathode is a nonopaque transparent cathode; a material of the cathode is a low work function metal or an alloy of low work function metal, and a film thickness is 10 nm-20 nm, or a material of the cathode is conductive oxide, and a film thickness is 10 nm-200 nm.

8. The OLED display according to claim 1, wherein a material of the hole injection layer is an organic small molecule hole injection material, a polymer hole injection material or a metal oxide hole injection material, and a film thickness is 1 nm-100 nm;
a material of the hole transporting layer is an organic small molecule hole transporting material or a polymer hole transporting material, and a film thickness is 10 nm-100 nm;
a material of the electron transporting layer is a metal complex material or an imidazole electron transport material, and a film thickness is 10 nm-100 nm;
a material of the electron injection layer is metal complex, alkali metal, alkali metal salts, alkali earth metal or alkali earth metal salts, and a film thickness is 0.5 nm-10 nm.

9. The OLED display according to claim 1, further comprising a sealant bonding the substrate and the cover plate.

10. An OLED display, comprising a substrate, a thin film transistor layer formed on the substrate, a blue light OLED formed on the thin film transistor layer, a cover plate located on the blue light OLED and laminated with the substrate and a color conversion layer formed at an inner side of the cover plate;
the blue light OLED comprising an anode, a hole injection layer, a hole transporting layer, a blue light emitting layer, an electron transport layer, an electron injection layer and a cathode which are stacked up from bottom to top in order;
the color conversion layer comprising a plurality of red conversion units and green conversion units which are separately located;
blue light emitted by the blue light emitting layer being respectively converted into red light by the red conversion units to emit, converted into green light by the green conversion units to emit and emitted through the cover plate, directly to realize color display;
both materials of the red conversion units and the green conversion units being organic metal halide perovskite materials;
the OLED display further comprising a sealant bonding the substrate and the cover plate;
wherein both materials of the substrate and the cover plate are glass or a flexible material;
wherein a material of the red conversion units is $CH_1NH_1Pb(I_{0.9}Br_{0.1})_3$, and a material of the green conversion units is $CH_3NH_3PbB_3$.

11. The OLED display according to claim 10, wherein a constitutional formula of the organic metal halide perovskite material is $CH_3NH_3PbA_3$, and A is a combination of one or more elements of Cl, Br and I.

12. The OLED display according to claim 10, wherein both materials of the red conversion units and the green conversion units are a combination of one or more of the organic metal halide perovskite materials;
the red conversion units and the green conversion units are single layer or multi layer structures;
a thickness of the red conversion units and the green conversion units is 10 nm-200 nm.

13. The OLED display according to claim 10, wherein a material of the blue light emitting layer is manufactured by doping a guest material in a host material, wherein a doping quality ratio of the host material and the guest material is 1:0.01-1;
the guest material is a blue light organic fluorescent material, and the host material is an anthracene derivative or a wide band gap organic material; or
the guest material is blue light organic phosphorescent material, and the host material is a wide band gap organic material.

14. The OLED display according to claim 10, wherein the anode is an opaque reflective type anode, comprising two conductive oxide layers and a reflective metal layer between the two conductive oxide layers, wherein a film thickness of the reflective metal layer is 50 nm-200 nm; a film thickness of the conductive oxide layers is 10 nm-50 nm.

15. The OLED display according to claim 10, wherein the cathode is a nonopaque transparent cathode; a material of the cathode is a low work function metal or an alloy of low work function metal, and a film thickness is 10 nm-20 nm, or a material of the cathode is conductive oxide, and a film thickness is 10 nm-200 nm.

16. The OLED display according to claim 10, wherein a material of the hole injection layer is an organic small molecule hole injection material, a polymer hole injection material or a metal oxide hole injection material, and a film thickness is 1 nm-100 nm;
a material of the hole transporting layer is an organic small molecule hole transporting material or a polymer hole transporting material, and a film thickness is 10 nm-100 nm;

a material of the electron transporting layer is a metal complex material or an imidazole electron transport material, and a film thickness is 10 nm-100 nm;
a material of the electron injection layer is metal complex, alkali metal, alkali metal salts, alkali earth metal or alkali earth metal salts, and a film thickness is 0.5 nm-10 nm.

* * * * *